United States Patent [19]

Nakazawa et al.

[11] Patent Number: 5,453,260
[45] Date of Patent: * Sep. 26, 1995

[54] AMORPHOUS SILICA OR SILICA-ALUMINA SPHERICAL PARTICLES AND PROCESS FOR PREPARATION THEREOF

[75] Inventors: Tadahisa Nakazawa, Tokyo; Masahide Ogawa, Niigata; Kiyoshi Abe, Niigata; Kazuhiko Suzuki, Niigata; Takashi Tokita, Niigata; Toshio Ito, Niigata, all of Japan

[73] Assignee: Mizusawa Industrial Chemicals, Ltd., Tokyo, Japan

[ * ] Notice: The portion of the term of this patent subsequent to Aug. 18, 2009 has been disclaimed.

[21] Appl. No.: 14,777

[22] Filed: Feb. 8, 1993

Related U.S. Application Data

[62] Division of Ser. No. 956,421, Oct. 2, 1992, Pat. No. 5,236,683, which is a continuation of Ser. No. 825,427, Jan. 22, 1992, abandoned, which is a continuation of Ser. No. 698,251, May 6, 1991, abandoned, which is a continuation of Ser. No. 145,586, Jan. 19, 1988, abandoned.

[30] Foreign Application Priority Data

Jan. 20, 1987 [JP] Japan ................................ 62-8915

[51] Int. Cl.$^6$ .............................. C01B 33/12; B01J 21/12
[52] U.S. Cl. .................. 423/327.1; 423/332; 423/335; 502/8; 502/10; 502/238
[58] Field of Search ................. 423/328.1; 502/263, 502/8; 428/402; 585/17

[56] References Cited

U.S. PATENT DOCUMENTS 5,139,760  8/1992  Ogawa et al. .................. 423/328.1
5,236,483  8/1993  Nakazawa et al. ............... 423/335

*Primary Examiner*—Anthony McFarlane
*Attorney, Agent, or Firm*—Spensley Horn Jubas & Lubitz

[57] ABSTRACT

Disclosed are amorphous silica or silica-alumina spherical particles composed of X-ray diffractometrically substantially amorphous silica or silica-alumina, wherein individual particles have a definite spherical shape and a notched surface, the circularity (A) represented by the following formula:

$$A = \frac{\sqrt{r1 \cdot r2}}{r1} \quad (1)$$

wherein r1 stands for the radius of the circumcircle of the profile of the particle in an electron microscope photo thereof and r2 stands for the radius of the inscribed circle of the profile of the particle in the electron microscope photo, is in the range of from 0.90 to 1, the notching degree (B) represented by the formula:

$$B = \frac{\Delta t}{r1} \times 100 \quad (2)$$

wherein $\Delta t$ stands for the depth between the peak and trough in the radial direction of notches on the profile of the particle in the electron microscope photo and r1 is as defined above, is in the range of from 1 to 10%, and the primary particle size (2r1) determined by the electron microscope method is in the range of from 0.1 to 20 μm.

5 Claims, 5 Drawing Sheets

AMORPHOUS SILICA OR SILICA-ALUMINA SPHERICAL PARTICLES AND PROCESS FOR PREPARATION THEREOF

This is a division of application Ser. No. 07/956,421, filed on Oct. 2, 1992, now U.S. Pat. No. 5,236,683, which is a file-wrapper continuation application of Ser. No. 07/825, 427, filed on Jan. 22, 1992, now abandoned, which is a file-wrapper continuation application of Ser. No. 07/698, 251, filed on May 6, 1991, now abandoned, which is a file-wrapper continuation application of Ser. No. 07/145, 586, filed on Jan. 19, 1988, now abandoned.

BACKGROUND OF THE INVENTION (1) Field of the Invention

The present invention relates to amorphous silica or silica-alumina spherical particles having a novel particulate shape and a process for the preparation thereof.

(2) Description of the Prior Art

Spherical particles of amorphous silica or silica-alumina are widely used as fillers for various films and other resins and rubbers, as fillers for cosmetics, as supporting carriers for perfumes and chemicals, as chromatography filler and for other purposes.

Spherical amorphous silica has been prepared according to the process in which a silica hydrosol is sprayed or the spray is further caused to impinge to a fluid, the process in which an organic silicic acid compound is hydrolyzed, the process in which a glass ceramic is molded into a spherical shape and is sintered, and the like process.

However, silica or silica-alumina spherical particles prepared according to these processes have a relatively coarse primary particle size and a broad particle size distribution. Therefore, development of silica or silica-alumina spherical particles having a fine primary particle size and a sharp particle size distribution is eagerly desired in the art.

When such spherical particles are used as a filler for a resin, the dispersibility of the particles in the resin and the compatibility of the particles with the resin should be taken into consideration. For example, when a resin having spherical particles incorporated therein is formed into a film or the like and is then drawn, a problem of formation of voids between the resin and the filler particles often arises.

SUMMARY OF THE INVENTION

It is therefore a primary object of the present invention to provide amorphous silica or silica-alumina particles having a novel particulate shape, in which the primary particle size is fine, the particles have a definite spherical shape and the particles have a notched surface, and a process for the preparation of these particles.

Another object of the present invention is to provide amorphous silica or silica-alumina particles which are excellent in the dispersibility in resins and the compatibility with resins and in which formation of voids between the particles and resins is prevented at various processing steps.

Still another object of the present invention is to provide amorphous silica or silica-alumina particles which have an excellent supporting property for various chemicals, perfumes and the like because of notches formed on the surfaces thereof.

In accordance with one aspect of the present invention, there are provided amorphous silica or silica-alumina spherical particles composed of X-ray diffractometrically substantially amorphous silica or silica-alumina, wherein individual particles have a definite spherical shape and a notched surface, the circularity (A) represented by the following formula:

$$A = \frac{\sqrt{r1 \cdot r2}}{r1} \quad (1)$$

wherein r1 stands for the radius of the circumcircle of the profile of the particle in an electron microscope photo thereof and r2 stands for the radius of the inscribed circle of the profile of the particle in the electron microscope photo, in the range of from 0.90 to 1, the notching degree (B) represented by the following formula:

$$B = \frac{\Delta t}{r1} \times 100 \quad (2)$$

wherein $\Delta t$ stands for the depth between the peak and trough in the radical direction of notches on the profile of the particle in the electron microscope photo and r1 is as defined above, is in the range of from 1 to 10%, and the primary particle size (2r1) determined by the electron microscope method is in the range of from 0.1 to 20 µm.

In accordance with another aspect of the present invention, there is provided a process for the preparation of amorphous silica or silica-alumina spherical particles, which comprises the step of synthesizing zeolite particles having an X-ray diffraction pattern inherent to P type zeolite, individual particles having a definite spherical shape as a whole and a notched surface, and the step of subjecting the zeolite particles to a one-staged or multiple-staged acid treatment to remove the sodium component or the sodium and alumina components sufficiently to render the zeolite amorphous.

DETAILED DESCRIPTION OF THE PREFERRED EMBODIMENTS

We succeeded in synthesizing zeolite particles having an X-ray diffraction pattern inherent to P type zeolite and having a definite spherical shape as a whole and a notched surface, and we found that if such zeolite particles are subjected to an acid treatment to remove the sodium component or the sodium and alumina components, spherical particles of amorphous silica or silica-alumina can be obtained.

The spherical particles of amorphous silica or silica-alumina according to the present invention are prominently characterized in that although the particles are composed of amorphous silica or silica-alumina, the particles have a definite spherical shape and the surfaces of the spherical particles are notched.

Figure 3:
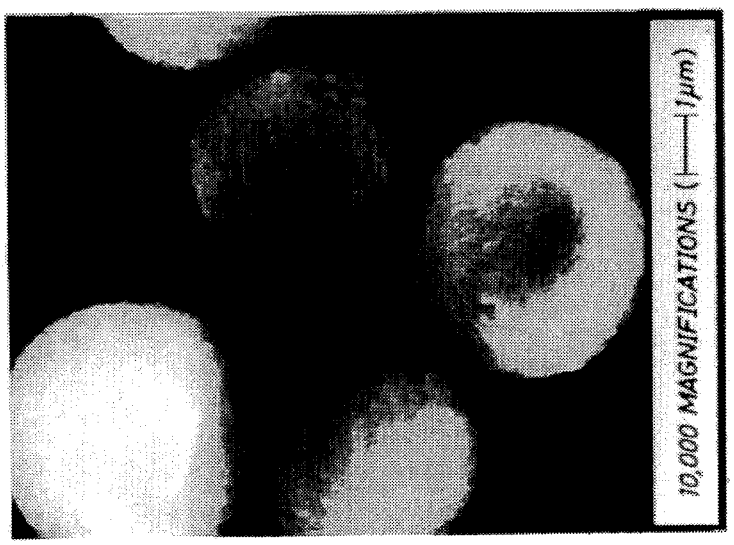
FIGS. 1, 2 and 3 are electron microscope photos of silica particles, silica-alumina particles and particles of starting P type zeolite, respective.
Figure 2:
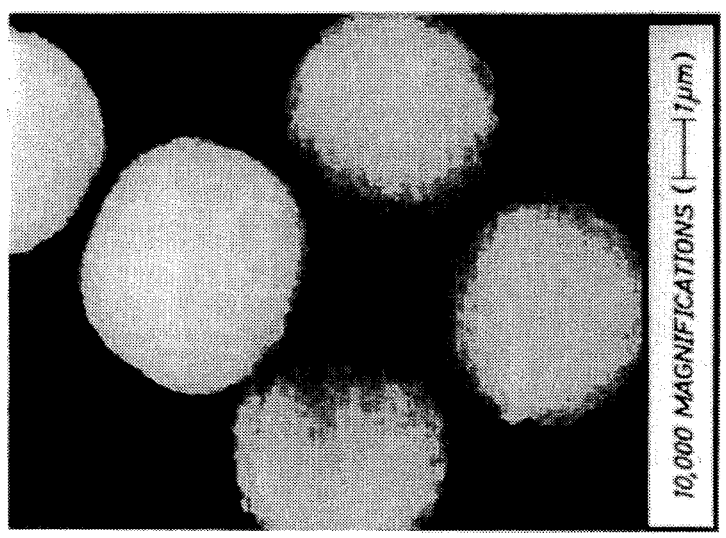
Figure 1:
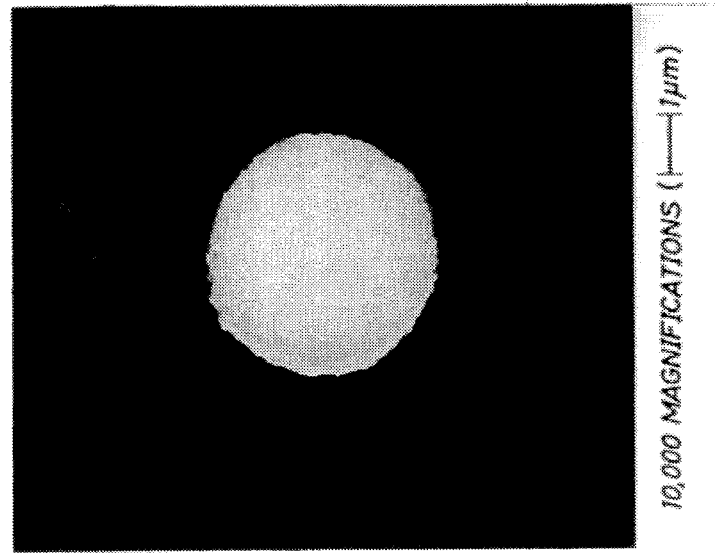

FIG. 1 of the accompanying drawing is an electron microscope photo (10,000 magnifications) of amorphous silica particles of the present invention. FIG. 2 is an electron microscope photo (10,000 magnifications) of amorphous silica-alumina particles of the present invention. FIG. 3 is an electron microscope photo (10,000 magnifications) of P type zeolite particles (used as the starting material).

From these electron microscope photos, surprising characteristic features of the present invention are understood. That is, it is seen that the spherical particles of amorphous silica or silica-alumina according to the present invention have a spherical shape resembling the true sphere as a whole as well as P type zeolite and they have a notched surface.

Figure 4:
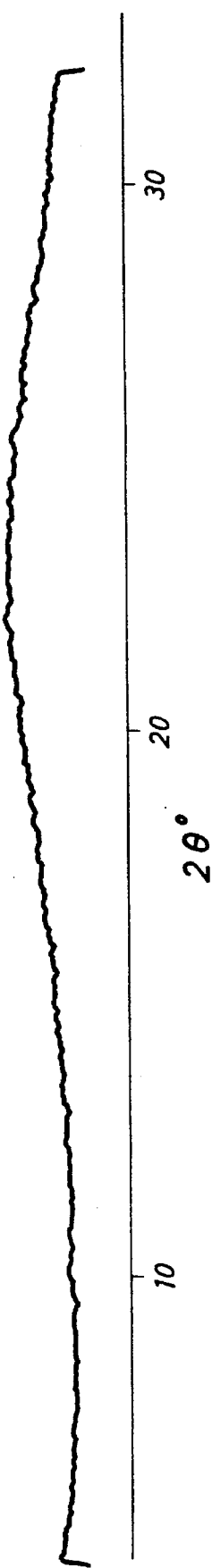
FIGS. 4, 5 and 6 are X-ray diffraction patterns of amorphous silica particles, amorphous silica-alumina particles and P type zeolite particles, respectively.
Figure 5:
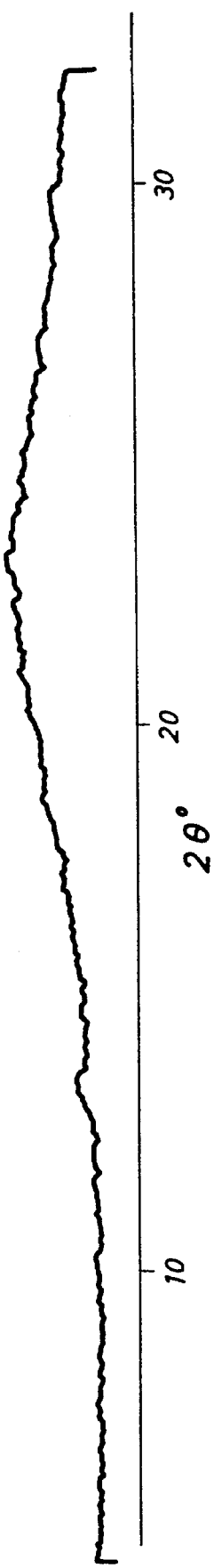
Figure 6:
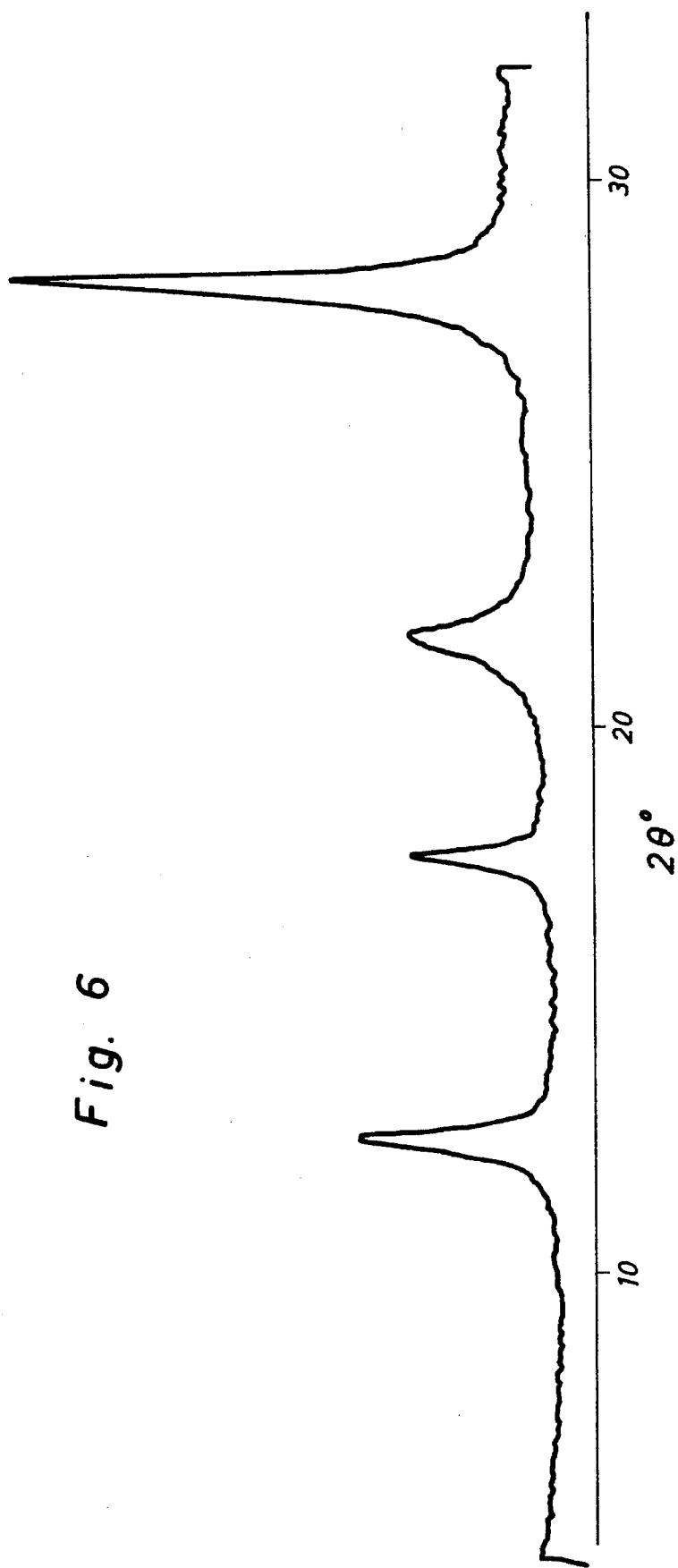
Figure 8:
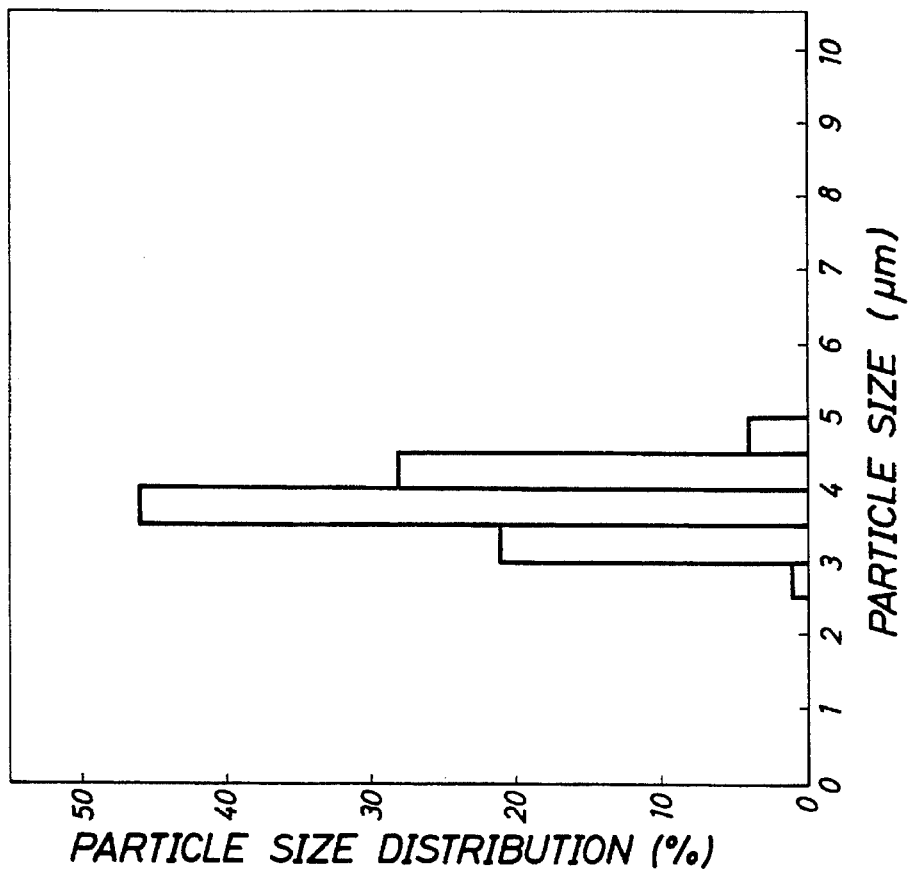
FIG. 8 is a histogram of the particle size distribution of spherical silica particles.

FIG. 4 shows an X-ray diffraction pattern (Cu-α) of the spherical amorphous silica particles shown in FIG. 1, FIG. 5 shows an X-ray diffraction pattern of the spherical amorphous silica-alumina particles shown in FIG. 2, and FIG. 6 shows an X-ray diffraction pattern of the P type zeolite particles shown in FIG. 3. From these X-ray diffraction patterns, it is seen that the product of the present invention has a particulate structure similar to that of the P type zeolite particles, but the product of the present invention is X-ray diffractometrically amorphous and is different from the P type zeolite particles in this point.

Figure 7:
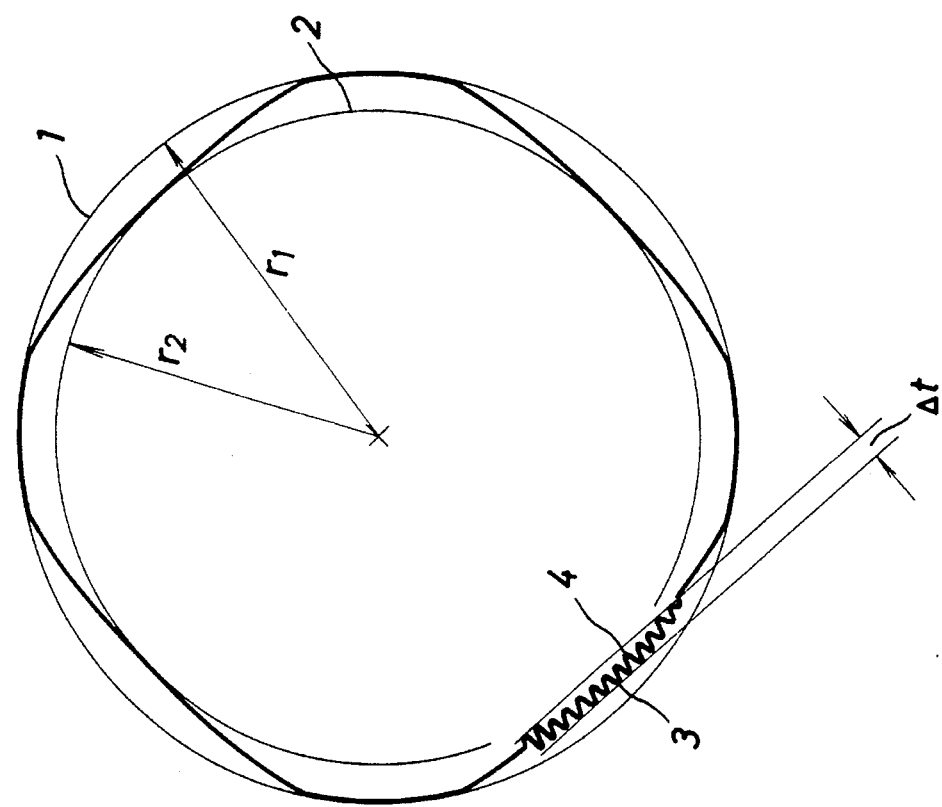
FIG. 7 shows the section of the projection of the peripheral profile of the particle according to the electron microscope method, in which r1 stands for the radius of the circumcircle 1, r2 stands for the radius of the inscribed circle 2 and reference numerals 3 and 4 represent the peak and trough in the radial direction of notches on the peripheral profile of the particle.

In FIG. 7 illustrating the circularity (A) and notching degree (B) mentioned in the instant specification, the section of the projection of the peripheral profile of the particle according to the electron microscope method is shown. The circumcircle 1 and inscribed circle 2 of this peripheral profile are drawn, and the circularity (A) is determined from the radius r1 of the circumcircle 1 and the radius r2 of the inscribed circle 2 according to the formula (1). This circularity (A) has the following meaning. Namely, in case of the true circle, since r1 is equal to r2, the circularity (A) is 1, and as the peripheral profile of the particle is deviated from the true circle, the difference between r1 and r2 is increased and the circularity (A) is smaller than 1. The notching degree (B) is determined from the depth Δt between the peak and trough in the radial direction of the notched profile of the particle according to the formula (2). This notching degree (B) is a value indicating the notch roughness of the surface.

In the particles of the present invention, the circularity (A) is in the range of from 0.90 to 1.0, especially from 0.95 to 1.0, and the notching degree (B) is in the range of from 1 to 10%, especially from 1.5 to 5%. This is another characteristic feature of the particles of the present invention. If the circularity (A) is too small and the below the above-mentioned range, the characteristics of spherical particles, such as good flowability and high bulk density, are lost and the dispersibility in resins or the like are degraded. The notching degree (B) has great influences on the interfacial properties between the particles and other substance when the particles are used in various fields. For example, when the particles of the present invention are incorporated into a resin and the composition is molded, since the resin is tightly engaged with the particles through the notched surfaces thereof, even if the molded film or the like is subjected to a drawing operation, formation of voids is controlled and a film excellent in the transparency can be obtained. If the notching degree (B) is too low and below the above-mentioned range, the compatibility with resins is degraded, and if the notching degree (B) exceeds the above-mentioned range, the strength of the particles per se is reduced or wearing of an apparatus or member falling in contact with the particles is increased. Moreover, if the notching degree (B) is within the above-mentioned range, when the particles are used as a carrier for agricultural chemicals or other chemicals, the supporting capacity is advantageously increased. This advantage is similarly attained when the spherical particles of amorphous silica or silica-alumina according to the present invention are used as a chromatography adsorbent.

In the spherical particles of amorphous silica or silica-alumina according to the present invention, the primary particle size (the particle size according to the electron microscope photo method, that is, 2r1) is in the range of from 0.1 to 20 μm, especially from 0.3 to 10 μm. Namely, the amorphous silica or silica-alumina particles of the present invention are characterized in that although individual particles have a definite spherical shape, the primary particle size is relatively small within the above-mentioned range. If the primary particle size is too small and below the above-mentioned range, secondary aggregation is readily caused and no good results can be obtained. If the primary particle size exceeds the above-mentioned range, the particles are not suitable as a resin filler.

The amorphous silica or silica-alumina of the present invention can be used either in the state where the primary particle size is very uniform and the particle size distribution is very sharp, or in the state where the primary particle size is distributed in a broad range, according to the intended object. In the former case, the standard deviation of the primary particle size in the spherical particles can be less than 0.85, especially less than 0.5.

The spherical particles of amorphous silica or silica-alumina according to the present invention are relatively dense, and the bulk density is generally in the range of from 0.2 to 1.2 g/ml and especially in the range of from 0.4 to 1.0 g/ml, though the bulk density differs to some extent according to the particle size. The BET specific surface of the spherical particles is smaller than 400 m$^2$/g, especially smaller than 300 m$^2$/g, though the BET surface area differs to some extent according to the particle size or the notching degree (B) of the surface.

The amorphous silica or silica-alumina of the present invention has the following composition by weight, though the composition differs to some extent according to the preparation process.

|  | General Range | Preferred Range |
| --- | --- | --- |
| $SiO_2$ | 60 to 99.99% | 70 to 99.99% |
| $Al_2O_3$ | 0 to 25% | 0 to 15% |
| $Na_2O$ | 0 to 12% | 0 to 4% |
| ignition loss | below 15% | below 13% |

When the spherical particles of the present invention are formed into an aqueous dispersion having a solid concentration of 1% by weight, the dispersion shows a pH value of 4.0 to 10, and this pH value is smaller than the pH value of the dispersion of the starting zeolite, which is larger than 11.

In accordance with one preferred embodiment of the present invention, there are provided amorphous silica-alumina spherical particles composed of X-ray diffractometrically substantially amorphous silica-alumina having an $SiO_2/Al_2O_3$ molar ratio of from 6 to 30 and an $Na_2O$ content lower than 2.0% by weight, wherein when the particles are held in an atmosphere maintained at a temperature of 25° C. and a relative humidity of 90% for 24 hours, the moisture absorption is lower than 13%. Since the particles of this type have a very low moisture absorption, when the particles are incorporated into a resin or rubber, blowing is controlled under processing conditions, and therefore, the particles are especially valuable as a filler for polymers.

In accordance with another preferred embodiment of the present invention, there are provided amorphous silica spherical particles composed of X-ray diffractometrically substantially amorphous silica having an $SiO_2$ content of at least 85% by weight, wherein when the particles are held in an atmosphere maintained at a temperature of 25° C. and a relative humidity of 90% for 24 hours, the moisture absorption is in the range of 5 to 25% by weight. Since the particles of this type have a higher moisture absorption and a higher surface activity than those of the above-mentioned amorphous silica-alumina spherical particles, the particles are especially valuable as a filler for cosmetics.

For this production of the amorphous silica or silica-alumina spherical particles of the present invention, at first, zeolite particles having an X-ray diffraction pattern inherent to P type zeolite, in which individual particles have a definite spherical shape as a whole and a notched surface, are prepared.

Of course, P type zeolite particles having a spherical shape are know. In the conventional synthesis processes, P type zeolite is formed as a by-product when X type zeolite and Y type zeolite are synthesized, and there is not known a process in which only P type zeolite in the form of spherical particles is efficiently synthesized.

We found that P type zeolite can be synthesized by mixing sodium silicate or active silicic acid gel, sodium aluminate and sodium hydroxide under the following molar ratio conditions to form a gel of an alkali metal alumino-silicate, homogenizing this gel and effecting crystallization at a temperature of 85° to 200° C. under atmospheric pressure or under hydrothermal conditions. P type Zeolite-Forming Ratios:

| Component Ratio | Ordinary Molar Ratio | Preferred Molar Ratio |
| --- | --- | --- |
| $Na_2O/SiO$ | 0.2 to 8 | 0.5 to 2.0 |
| $SiO_2/Al_2O_3$ | 3 to 20 | 4 to 10 |
| $H_2O/Na_2O$ | 20 to 200 | 30 to 100 |

The formed zeolite is washed with water, the classifying operation is carried out so that a desired particle size is obtained, and the zeolite is then subjected to an acid treatment described below.

In the present invention, in order to prepare amorphous silica or silica-alumina particles having a high circularity (A), it is preferred that P type zeolite be used as the starting material. The chemical composition of this starting P type zeolite is as follows.

Chemical Compositions of P Type Zeolite $SiO_2$: 40 to 70% by weight $Al_2O_3$: 15 to 30% by weight $Na_2O$: 8 to 20% by weight $H_2O$: 0 to 20% by weight From the above chemical composition, it is seen that the starting zeolite used in the present invention is advantageous in that since the $SiO_2/Al_2O_3$ ratio is high, the amount of the $Al_2O_3$ component to be removed is small.

According to the present invention, the above-mentioned zeolite particles are subjected to a one-staged or multiple-staged acid treatment to remove the sodium component or the sodium and alumina components sufficiently to render the zeolite amorphous. It was found that if at least 0.3 mole %, especially at least 0.5 mole %, of the $Na_2O$ component is removed in P type zeolite, the particles are rendered X-ray diffractometrically amorphous. Accordingly, if the sodium component is removed in an amount exceeding the above-mentioned lower limit, spherical silica-alumina particles can be obtained, and if the alumina component is further removed by the acid treatment, spherical silica particles can be obtained.

Either an inorganic acid or an organic acid can be used for the acid treatment without any limitation. From the economical viewpoint, use of a mineral acid such as hydrochloric acid, sulfuric acid, nitric acid or phosphoric acid is preferred. The acid is preferably used in the form of an aqueous solution for neutralization of the zeolite or elution of the alumina component.

It is preferred that the acid treatment be performed by forming an aqueous slurry of the crystalline zeolite and adding the acid to the slurry. As the acid is added, the pH value is shifted to the acidic side, and as the neutralization is advanced, the pH value is shifted to the alkaline side again and the pH value becomes saturated. It is preferred that the neutralization be effected so that the saturated pH value is 2.0 to 7.0, especially 3.5 to 7.0. If this saturated pH value exceeds the above-mentioned range, it is difficult to remove the alkali component from the zeolite so that the zeolite is rendered amorphous. If the saturated pH value is below the above-mentioned range, it is difficult to perform the acid treatment while maintaining the predetermined shape in the formed particles. As regards other acid treatment conditions, it is preferred that the temperature be 20° C. to 100° C., and the concentration of the zeolite particles in the slurry is preferably 5 to 30% by weight.

The acid treatment may be conducted in one stage or two or more stages. For example, in the case where only the sodium component is removed, a one-staged treatment is sufficient, and in the case where the alumina component is removed as well as the sodium component, a multiple-staged treatment such as a two- or three-stage treatment is effective. In the latter case, there is preferably adopted a method in which the sodium component in the zeolite is removed by the first heat treatment and the acid-treated product is dried or calcined and then subjected to the subsequent heat treatment to remove at least a part of the alumina component. The intermediate drying or calcining treatment is performed so as to prevent disintegration of the particles at the subsequent heat treatment. It is considered that this effect is due to the shrinkage of the particles caused by drying or calcining.

The obtained amorphous silica or silica-alumina spherical particles are washed with water, dried and calcined to obtain a final product.

When the water absorption is measured after the particles are held in an amorphous maintained at a temperature of 25° C. and a relative humidity of 90% for 24 hours, the water absorption of starting P type zeolite is 20 to 25% by weight, which is a level inherent to the zeolite. In contrast, the water absorption, determined under the same conditions, of the amorphous silica-alumina of the present invention is smaller 13% by weight, and the water absorption of the silica of the present intention is 5 to 25% by weight. This means that when the spherical particles of the present invention are incorporated into various resins, especially thermoplastic resins, blowing owing to absorbed water is controlled at the molding step and also in this point, the spherical particles of the present invention are advantageous as a resin filler.

The spherical particles of the present invention are preferably surface-treated or surface-coated with metal soaps, resin acid soaps, resins or waxes, silane or titanium type coupling agents or silica according to need.

The amorphous silica or silica-alumina spherical particles of the present invention can be incorporated in various resins, for example, olefin resins such as polypropylene, polyethylene, a crystalline propylene/ethylene copolymer, an ion-crosslinked olefin copolymer and an ethylene/vinyl acetate copolymer, thermoplastic polyesters such as polyethylene terephthalate and polybutylene terephthalate, polyamides such as 6-nylon and 6,6-nylon, chlorine-containing resins such as a vinyl chloride resin and a vinylidene chloride resin, polycarbonates, polysulfones and polyacetals, and a good slipping property or anti-blocking property can be imparted to molded articles of these resins, for example, biaxially drawn films.

Furthermore, the spherical particles of the present invention can be used as a filler or reinforcer for molding thermosetting resins or coating-forming paints or as a ceramic substrate.

Moreover, the spherical particles of the present invention can be used as an inorganic filler for an electroviscous liquid comprising an electroconductive oil and an inorganic dispersed substance, which is used for a clutch, a hydraulic pressure valve, a shock-absorbing system and the like.

Still in addition, the spherical particles of the present invention are valuable as carriers for supporting cosmetic bases such as powder foundation, liquid (paste) foundation, baby powder and cream, medicines, agricultural chemical, perfumes, aromatic agents and the like, and can be used as a carrier for various chromatographies.

The present invention will now be described in detail with reference to the following examples that by no means limit the scope of the invention.

EXAMPLE 1

By using commercially available water glass of the reagent grade (sodium silicate No. 3, $SiO_2$=27% by weight, $Na_2$=9.0% by weight), sodium aluminate ($Al_2O_3$=22.5% by weight, $Na_2O$=15.5% by weight) and caustic soda, a dilute solution of sodium silicate and a solution of sodium aluminate were prepared so that the entire amount was 16 kg and the following molar ratios were attained:

$Na_2O/SiO_2$=0.7, $SiO_2/Al_2O_3$=8.8, and $H_2O/Na_2O$=80.

In a stainless steel vessel having an inner volume of about 25 l, 8.3 kg of the aqueous solution of sodium silicate was gradually mixed with 7.8 kg of the dilute solution of sodium aluminate with stirring to form an entirely homogeneous gel of sodium aluminosilicate. Then, the temperature of the sodium aluminosilicate gel was elevated to 90° C. with violet stirring and at this temperature, crystallization was effected over a period of 48 hours.

Then, the solid was separated from the mother liquor by suction filtration and the solid was sufficiently washed with water to obtain about 1.7 kg of a P type zeolite cake having a solid concentration of 43% by weight. Water was added to the cake so that the solid concentration was 10% by weight, and the solid was sufficiently dispersed. Classification was repeated several times by using a small liquid cyclone to from a starting material to be subjected to the first stage acid treatment. The so-obtained slurry was dried in an oven maintained at 80° C. for 24 hours. The electron microscope photo of the dried product is shown in FIG. 3 and an X-ray diffraction pattern of the dried product is shown in FIG. 6. Furthermore, the properties and chemical composition of the obtained powder (sample 1-1) are shown in Table 1. Then 3 l of the wet-classified slurry was charged in a beaker having an inner volume of 5 l, and about 1.3 l of dilute sulfuric acid diluted to a concentration of 10% by weight was gradually added with stirring. After the addition, the mixture was stirred for 1 hour and the solid was separated from the mother liquor by suction filtration. The solid was sufficiently washed with water and the cake was dried in and electric thermostat drier maintained at 80° C. for 24 hours. The X-ray diffraction pattern of the dried product is shown in FIG. 2. The properties and chemical composition of the powder (sample 1-2) are shown in Table 1. Then, about 300 g of the dried powder was calcined at 450° C. for 2 hours and naturally cooled. Then, 200 g of the calcined powder was charged in a beaker having an inner volume of 2 l, and 1,200 ml of water was added thereto and the mixture was stirred and dispersed for 30 minutes by a magnetic stirrer.

Then 110 or 270 ml of sulfuric acid of the reagent grade diluted to 50% by weight, this amount being 2 or 5 moles per mole of the sum of $Al_2O_3$ and $Na_2O$ in the powder, was gradually added to the dispersion. At this point, the temperature was elevated to about 90° C. Stirring was conducted for 30 minutes after the addition of sulfuric acid, and the temperature was gradually elevated and the treatment was carried out at 98° C. for 2 hours.

The solid was separated from the mother liquor by suction filtration, and the solid was sufficiently washed with pure water in an amount 5 times the amount of the mother liquor to obtain a cake of spherical silica particles. Then, the cake was dried in an electric thermostat drier maintained at 110° C. for 24 hours and pulverized according to customary procedures using a sample mill to obtain a powder of spherical silica particles. The properties and chemical composition of the so-obtained powder (sample 1-3 or 1-4) are shown in Table 1.

Figure 10:
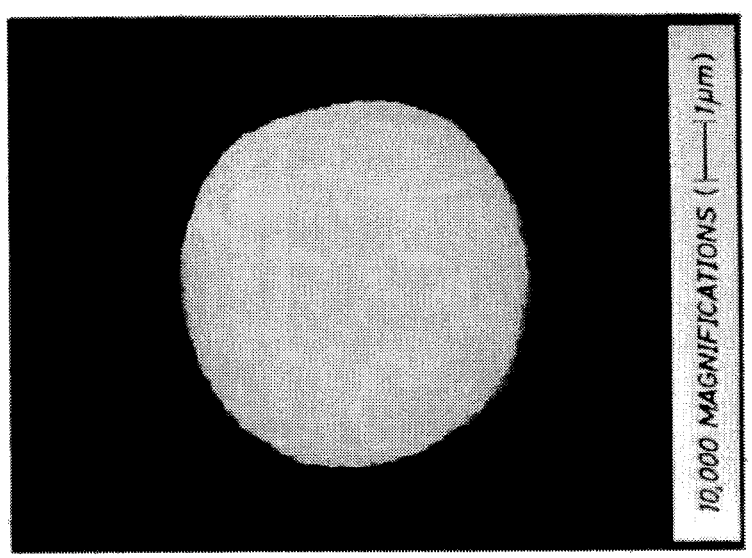

An electron microscope photo of the powder (sample 1-4) after calcination at 450° C. for 2 hours was taken, and the sizes of 100 particles in the photo were measured. The obtained particle size distribution is shown in FIG. 10. The standard deviation ($\sigma$) was 0.418. A typical electron microscope photo of the particles is shown in FIG. 1. From these photos, the circularity (A) was determined according to the following formula with respect to 5 points:

$$A = \frac{\sqrt{r1 \cdot r2}}{r1}$$

wherein r1 stands for the radius (μm) of the circumcircle and r2 stands for the radius (μm) of the inscribed circle.

The obtained results are shown in Table 2.

Furthermore, from the electron microscope photos, the notching degree (B) was determined according to the following formula with respect to 5 points:

$$B = \frac{\Delta t}{r1} \times 100$$

wherein Δt stands for the depth (μm) between the peak and trough on the periphery and r1 stands for the radius (μm) of the circumcircle.

The obtained results are shown in Table 2.

Measurement Methods

In the examples, (1) the pack density, (2) the specific surface area, (3) the oil absorption, (4) the whiteness, (5) the pH value, (6) the particle size by an electron microscope, (7) the X-ray diffractometry, (8) the chemical composition, (9) the moisture absorption and (10) the average particle size were determined according to the following methods.

(1) Pack Density

The pack density was determined according to the method of JIK K-6620 6–8.

(2) Specific Surface Area

The specific surface area was measured by the BET method using Sorptomatic Series 1800 supplied by Caeroeruba Co.

(3) Oil Absorption

The oil absorption was determined according to the method of JIS P-8123.

(4) Whiteness

The whiteness was determined according to the method of JIS P-8123.

(5) pH Value

The pH value was measured according to the method of JIS K-5101 24A.

(6) Particle Size by Electron Microscope

An appropriate amount of a sample fine powder was placed on a metal sheet and was sufficiently dispersed, and the powder was metal-coated by a metal coating apparatus (Ion Sputter Model E-101 supplied by Hitachi) to obtain a sample to be photographed. Several electron microscope photographic images were obtained while changing the visual field according to customary procedures using a scanning type electron microscope (Model S-570 supplied by Hitachi). A typical particle image was selected among the spherical particle images of each visual field and the diameter of the spherical particle image was measured and indicated as the primary particle size in the instant specification.

(7) X-ray Diffractometry

A sample was first passed through a 200-mesh Tyler standard sieve and dried in an electric thermostat drier maintained at 80° C. for 5 hours. Then, the sample was naturally cooled in a desiccator and the X-ray diffractometry was carried out under the following conditions to identify the crystal form.

Apparatus

X-ray diffraction apparatus supplied by Rigaku Denki, provided with goniometer PMG-S2 and rate meter ECP-D2.

Measurement Conditions

Target: Cu
Filter: Ni
Voltage: 35 kV
Current: 20 mA
Full scale of counting: $4 \times 10^3$ C/S
Time constant: 1 second
Chart speed: 1 cm/min
Scanning speed: 1°/min
Diffraction angle: 1°
Slit width: 0.15 mm
Measurement range: 2θ=5° to 40°

(8) Chemical Composition

The ignition loss (Ig-loss), silicon dioxide ($SiO_2$), aluminum oxide ($Al_2O_3$) and sodium oxide ($Na_2O$) were determined according to the method of JIS M-8852. When the contents of aluminum oxide and sodium oxide were traces, the atomic adsorption spectroscopy method was adopted in combination.

(9) Moisture Absorption

A weighting bottle of 40 mm×40 mm, the weight of which had been measured, was charged with about 1 g of the sample, and the sample was dried in an electric thermostat drier maintained at 150° C. for 3 hours and was then naturally cooled in a deciccator. Then, the weight of the sample was precisely measured and was charged in a disiccator, the relative humidity of which had been adjusted to 90% in advance with sulfuric acid. The weight increase after 24 hours was measured and this weight increase was designated as the moisture absorption.

(10) Average Particle Size

Precisely weighed 1 g of the sample was charged in a beaker having an inner volume of 200 ml, and 150 ml of deionized water was added thereto. The sample was dispersed with stirring under ultrasonic vibration. The accumulated particle size distribution was determined by a Colter counter (Model TAII) and an aperture tube 50μ, and the average particle size was determined from the accumulated particle size distribution diagram.

TABLE 1

| Sample No. | 1-1 | 1-2 | 1-3 | 1-4 |
|---|---|---|---|---|
| Pack density (g/ml) | 0.77 | 0.76 | 0.79 | 0.81 |
| Specific surface area (BET method) (m²/g) | — | 31 | 195 | 283 |

TABLE 1-continued

| Sample No. | 1-1 | 1-2 | 1-3 | 1-4 |
|---|---|---|---|---|
| Oil absorption (ml/100 g) | 46 | 46 | 48 | 58 |
| Whiteness (Hunter reflection method) (%) | 96.6 | 96.5 | 96.4 | 96.8 |
| pH Value of 5% suspension (−/25° C.) | 10.9 | 8.9 | 7.8 | 4.8 |
| Particle size (μm) by electron microscope | 4.5, truly spherical | 4.0, truly spherical | 4.0, truly spherical | 3.8, truly spherical |
| Crystal form by X-ray diffractometry | Pc form | amorphous | amorphous | amorphous |
| Chemical Composition (% by weight) (based on product dried at 110° C.) | | | | |
| Ig-loss | 11.77 | 9.51 | 9.32 | 7.38 |
| $SiO_2$ | 51.88 | 56.72 | 76.5 | 92.46 |
| $Al_2O_3$ | 22.66 | 24.95 | 10.2 | 0.18 |
| $Na_2O$ | 13.60 | 8.76 | 3.70 | 0.0 |
| Total | 99.91 | 99.94 | 99.72 | 100.03 |
| $SiO_2/Al_2O_3$ molar ratio | 3.89 | 3.86 | 7.5 | 8.73 |
| Moisture absorption (% by weight) (90% RH × 24 hours)*1 | 19.1(12.5) | 9.6(4.3) | 9.8(5.1) | 22.7(14.6) |
| Yield (%)*2 | 100 | 93.6 | 88.2 | 63.2 |
| Average particle size ($D_{50}$) (μm) | 4.7 | 4.3 | 4.1 | 3.9 |

Note
*1: the parenthesized value indicates the moisture absorption of powder calcined at 500° C. for 1 hour
*2: the yield was calculated from the amount of obtained powder as the anhydride

TABLE 2

| Radius r1 (mm) of circumcircle | Radius r2 (mm) of inscribed circle | Depth Δt (mm) between peak and through | Circularity (A) | Notching degree (B) | Remarks |
|---|---|---|---|---|---|
| 19.35 | 18.10 | 0.8 | 0.967 | 4.1% | FIG. 1 |
| 18.50 | 17.55 | 0.6 | 0.974 | 3.2% | |
| 19.00 | 18.50 | 0.4 | 0.987 | 2.1% | |
| 21.10 | 19.75 | 0.6 | 0.967 | 2.8% | |
| 18.85 | 18.40 | 0.9 | 0.988 | 4.8% | |
| ← mean value → | | | 0.9766 | 3.4% | |

Comparative Example 1

The slurry of sample 1-1 prepared in Example 1, the product obtained by drying this slurry in an electric thermostat drier maintained at 80° C. for 24 hours and the product obtained by calcining this dried product at 500° C. for 2 hours were treated with sulfuric acid in an amount of 5 moles per mole of the sum of $Al_2O_3$ and $Na_2O$ in the same manner as described in Example 1. In any of these samples, spherical silica could not be obtained in a yield higher than 1%.

EXAMPLE 2

A finely divided silicic acid gel obtained by acid-treating acid clay produced at Nakajo, Niigata Prefecture, Japan, which is a clay of the smectite group, was prepared as the starting silicate component. The process for the preparation of this silicic acid gel is described below.

It was found that the acid clay produced at Nakajo, Niigata Prefecture, Japan contains 45% by weight of water in the natural state, and the main components are 72.1% by weight of $SiO_2$, 14.2% by weight of $Al_2O_3$, 3.87% by weight of $Fe_2O_3$, 3.25% by weight of MgO, 1.06% by weight of CaO and 3.15% by weight of the ignition loss based on the dry product (dried at 110° C.). This starting acid clay was molded in columns having a diameter of 5 mm and a length of 5 to 20 mm. Then, 1250 kg (as the dry product) of the molded clay was charged in a lead-lined wood tank having a capacity of 5 m³, and 3300 l of an aqueous solution of sulfuric acid having a concentration of 47% by weight was added thereto and the mixture was heated at 90° C. Thus, the clay was acid-treated in the granular state for 40 hours, and the sulfate of the basic component reacted with sulfuric acid was removed by decantation washing using a dilute aqueous solution of sulfuric acid and water. Then, the residue was washed with water until the sulfuric radical was not detected, whereby a granular acid-treated product was obtained.

The results of the analysis of the chemical composition of the acid-treated product after drying at 110° C. for 2 hours are as follows.

Ignition loss (1000° C.×1 hour): 3.75% by weight $SiO_2$: 94.34% by weight $Al_2O_3$: 1.16% by weight $Fe_2O_3$: 0.16% by weight MgO: 0.18% by weight The concentration of the above-mentioned active silicic acid gel was adjusted to 20% by weight, and the gel was wet-pulverized by a ball mill to obtain the starting silicic acid component.

By using the above-mentioned active silicic acid gel slurry, sodium aluminate of the reagent grade ($Al_2O_3$=22.5% by weight, $Na_2O$=15.5% by weight) and sodium hydroxide, a dilute active silicic acid gel slurry and a dilute solution of sodium aluminate were prepared so that the entire amount was 16 kg and the following molar ratios were attained:

$Na_2O/SiO_2$=0.55, $SiO_2/Al_2O_3$=6.0, and $H_2O/Na_2O$=65.

In the same manner as described in Example 1, the crystallization was carried out and the classification was performed by using a liquid cyclone to obtain a starting material to be subjected to the first stage acid treatment (sample 1-1).

The properties and chemical composition of the so-obtained powder are shown in Table 3. The primary particle size determined by an electron microscope was about 1.5 μm, and it was found that the powder was composed of spherical particles excellent in the dispersibility.

Then, the powder was subjected to the first stage acid treatment and dried in the same manner as described in Example 1. The properties and chemical composition of the obtained powder (sample 2-2) are shown in Table 3.

Figure 9:
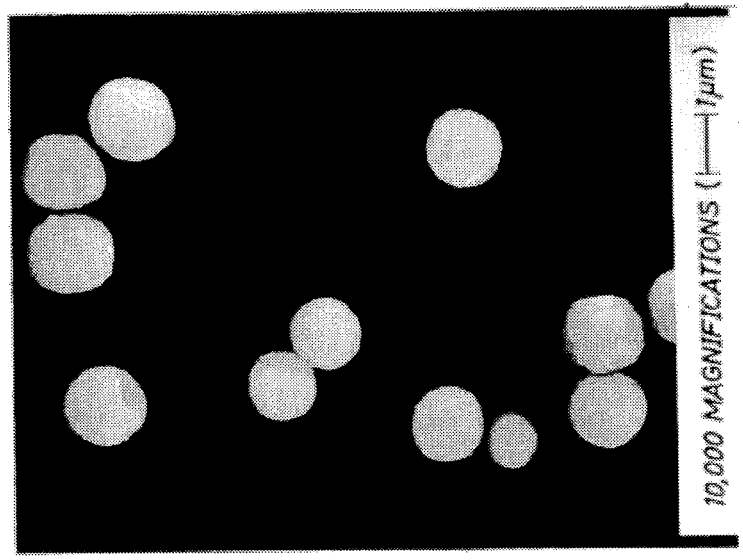

The dried powder was calcined at 450° C. for 2 hours and subjected to the second stage acid treatment by using sulfuric acid in an amount of 3.8 or 5 moles per mole of the sum of $Al_2O_3$ and $Na_2O$ in the same manner as described in Example 1, followed by water washing. An electron microscope photo (10,000 magnifications) of the powder (sample 2-3 or 2-4) obtained by drying the cake is shown in FIG. 9. The properties and chemical compositions of the powder are shown in Table 3. In the same manner as described in Example 1, the circularity (A) and notching degree (B) were determined from an enlarged photo of 30,000 magnifications with respect to five points.

Comparative Example 2

The slurry of sample 2-1 prepared in Example 2, a product obtained by drying this slurry in an electric thermostat drier maintained at 80° C. for 24 hours and a product obtained by calcining this dried product at 500° C. for 2 hours were subjected to the second stage acid treatment (with sulfuric acid in an amount of 5 moles per mole of $Al_2O_3$ and $Na_2O$) in the same manner as described in Example 1. In any of these samples, spherical silica could not be obtained in a yield higher than 0.5%.

EXAMPLE 3

P type zeolite was synthesized in the same manner as described in Example 1 except that the synthesis molar ratios were changed as follows:

$Na_2O/SiO_2$=0.7, $SiO_2/Al_2O_3$=8.0, and $H_2O/Na_2O$=100.

The primary particle size of this zeolite was about 7 μm and it was found that the zeolite was composed of spherical particles excellent in the dispersibility. The properties and chemical composition of the powder (sample 3-1) are shown in Table 5.

The properties and chemical composition of a product (sample 3-2) obtained by subjected the particles to the first

TABLE

| Sample No. | 2-1 | 2-2 | 2-3 | 2-4 |
|---|---|---|---|---|
| Pack density (g/ml) | 0.52 | 0.56 | 0.54 | 0.53 |
| Specific surface area (BET method) ($m^2/g$) | — | 38 | 200 | 320 |
| Oil absorption (ml/100 g) | 50 | 51 | 57 | 62 |
| Whiteness (Hunter reflection method) (%) | 96.1 | 96.0 | 96.4 | 95.3 |
| pH Value of 5% suspension (−/25° C.) | 11.20 | 8.64 | 6.7 | 4.62 |
| Particle size (μm) by electron microscope | 1.5, truly spherical | 1.2, truly spherical | 1.3, truly spherical | 1.2, truly spherical |
| Crystal form by X-ray diffractometry | Pc form | amorphous | amorphous | amorphous |
| Chemical Composition (% by weight) (based on product dried at 110° C.) | | | | |
| Ig-loss | 11.74 | 11.21 | 7.80 | 6.90 |
| $SiO_2$ | 51.18 | 56.21 | 84.8 | 92.86 |
| $Al_2O_3$ | 22.96 | 24.88 | 6.73 | 0.21 |
| $Na_2O$ | 14.02 | 7.69 | 0.61 | 0.01 |
| Total | 99.90 | 99.99 | 99.94 | 99.98 |
| $SiO_2/Al_2O_3$ molar ratio | 3.79 | 3.84 | 12.6 | 7.52 |
| Moisture absorption (% by weight) (90% RH ×24 hours)*1 | 19.7(14.3) | 10.9(5.9) | 12.3(6.4) | 21.3(15.1) |
| Yield (%)*2 | 100 | 90.8 | 76.5 | 58.1 |
| Average particle size ($D_{50}$) (μm) | 1.82 | 1.67 | 1.64 | 1.63 |

*1: the parenthesized value indicates the moisture absorption of powder calcined at 500° C. for 1 hour
*2: the yield was calculated from the amount of obtained powder as the anhydride

TABLE 4

| Circularity (A) | Notching Degree (B) | Remarks |
|---|---|---|
| 0.981 | 2.4% | mean value of 5 points | stage acid treatment in the same manner as described in Example 1 are shown in Table 5. An electron microscope photo of a powder (sample 3-3) obtained by subjecting the above product to the second stage acid treatment is shown in FIG. 10. The properties and chemical composition of the powder are shown in Table 5.

The circularity (A) and notching degree (B) determined in the same manner as described in Example 1 were 0.989 and 1.8%, respectively.

TABLE 5

| Sample No. | 3-1 | 3-2 | 3-3 |
|---|---|---|---|
| Pack density (g/ml) | 0.87 | 0.94 | 0.94 |
| Specific surface area (BET method) ($m^2/g$) | — | 29 | 303 |
| Oil absorption (ml/100 g) | 20 | 18 | 20 |

TABLE 5-continued

| Sample No. | 3-1 | 3-2 | 3-3 |
|---|---|---|---|
| Whiteness (Hunter reflection method) | 911.8 | 94.8 | 95.2 |
| pH Value of 5% suspension (–/25° C.) | 10.9 | 7.9 | 4.5 |
| Particle size (μm) by electron microscope | about 7μ, truly spherical | about 6.5μ, truly spherical | about 6μ, truly spherical |
| Crystal form by X-ray diffractometry | Pc form | amorphous | amorphous |
| Chemical Composition (% by weight) (based on product dried at 110° C.) | | | |
| Ig-loss | 11.00 | 10.69 | 81.15 |
| $SiO_2$ | 52.05 | 56.21 | 91.52 |
| $Al_2O_3$ | 23.41 | 25.13 | 0.37 |
| $Na_2O$ | 13.81 | 7.94 | 0.01 |
| Total | 100.27 | 99.97 | 100.05 |
| $SiO_2/Al_2O_3$ molar ratio | 3.78 | 3.80 | 421 |
| Moisture absorption (L% by weight) (90% RH × 24 hours)*1 | 18.4(13.1) | 10.2(4.1) | 20.96(15.1) |
| Yield (%)*2 | 100 | 93.7 | 62.1 |
| Average particle size ($D_{50}$) (μm) | 7.8 | 7.0 | 6.7 |

Note?
*1: the parenthesized value indicates the moisture absorption of powder calcined at 500° C. for 1 hour
*2: the yield was calculated from the amount of obtained powder as the anhydride

EXAMPLE 4

By using commercially available water glass of the reagent grade (sodium silicate No. 3, $SiO_2$=27% by weight, $Na_2O$=9.0% by weight), sodium aluminate ($Al_2O_3$=22.5% by weight, $Na_2O$=15.5% by weight) and sodium hydroxide, a dilute solution of sodium silicate and a dilute solution of sodium aluminate were prepared so that the entire amount was 1.5 kg and the following molar ratios were attained:

$Na_2O/SiO_2$=0.7,
$SiO_2/Al_2O_3$=8.0, and
$H_2O/Na_2O$=80.

In a stainless steel vessel having an inner volume of about 2 l, 780 g of a dilute solution of sodium silicate was gradually mixed with 730 g of a dilute solution of sodium aluminate with stirring to obtain a sodium aluminosilicate gel which was homogeneous as a whole.

Then, this sodium aluminosilicate gel was charged in a small pressure vessel (Model TEM-U supplied by Taiatsu Glass Kogyo) having an inner volume of about 1.2 l, and the temperature was elevated to 125° C. with stirring and crystallization was effected at this temperature for 6 hours. The pressure at this crystallization was about 2 kg/cm²-G. Then, the slurry was taken out from the vessel and the solid was separated from the mother liquid by suction filtration. The solid was sufficiently washed with water to obtain 120 g of a cake of P type zeolite having a solid concentration of 45% by weight.

The primary particle size of the zeolite by an electron microscope was about 1.0 μm. The properties an chemical composition of the powder (sample 4-1) are shown in Table 6.

Then, 50 g of the powder was charged in a beaker having a capacity of 1 l and 500 ml of water was added thereto, and 90 ml of sulfuric acid diluted to 10% by weight was gradually added to the mixture with stirring by a magnetic stirrer. Then, the first stage acid treatment was carried out in the same manner as described in Example 1 to obtain 40 g of an acid-treated powder (sample 4-2). The properties and chemical composition of the powder are shown in Table 6.

Then, the dry powder was calcined at 450° C. for 2 hours and naturally cooled, and 40 g of the calcined powder was charged in a beaker having a capacity of 1 l and 600 ml of water was added to the powder. The powder was sufficiently stirred by a magnetic stirrer, and diluted sulfuric acid (50% by weight) was added in an amount of 5 moles per mole of the sum of $Al_2O_3$ and $Na_2O$ in the powder and the treatment was conducted at 98° C. for 2 hours.

The post treatment was carried out in the same manner as described in Example 1 to obtain about 20 g of spherical silica particles (sample 4-3) having a primary particle size of about 0.8 μm as measured by an electron microscope.

Figure 11:
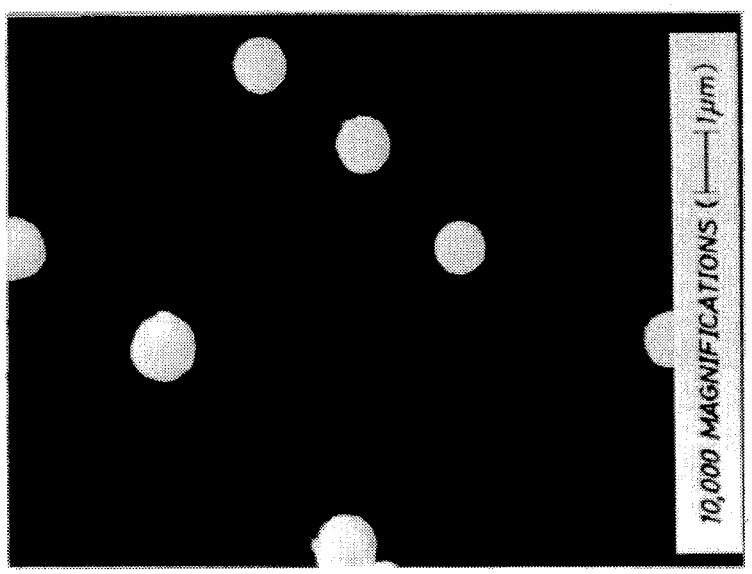
FIGS. 9, 10 and 11 are electron microscope photos of spherical particles having particle sizes of 1.2 um, 6.0 um, and 0.8 um, respectively.

The electron microscope of the spherical particles is shown in FIG. 11, and the properties and chemical composition of the powder are shown in Table 6.

TABLE 6

| Sample No. | 4-1 | 4-2 | 4-3 |
|---|---|---|---|
| Pack density (g/ml) | 0.43 | 0.41 | 0.38 |
| Specific surface area (BET method) (m²/g) | — | 81 | 320 |
| Oil absorption (ml/100 g) | 50 | 55 | 61 |
| Whiteness (Hunter reflection method) (%) | 95.4 | 95.6 | 95.1 |
| pH Value of 5% suspension (–/25° C.) | 11.2 | 8.8 | 4.5 |
| Particle size (μm) by electron microscope | 1.0, truly spherical | 0.8, truly spherical | 0.8, truly spherical |
| Crystal form by X-ray diffractometry | Pc form | amorphous | amorphous |
| Chemical Composition (% by weight) (based on product dried at 110° C.) | | | |
| Ig-loss | 12.13 | 1045 | 9.08 |

TABLE 6-continued

| Sample No. | 4-1 | 4-2 | 4-3 |
|---|---|---|---|
| $SiO_2$ | 51.73 | 56.61 | 90.72 |
| $Al_2O_3$ | 23.00 | 25.01 | 0.21 |
| $Na_2O$ | 13.88 | 7.91 | 0.01 |
| Total | 100.74 | 99.98 | 100.02 |
| $SiO_2/Al_2O_3$ molar ratio | 3.82 | 3.85 | 734 |
| Moisture absorption (% by weight) (90% RH × 24 hours)*1 | 19.0 | 9.1 | 23.1 |
| Yield (%)*2 | 100 | 88.3 | 51.3 |
| Average particle size ($D_{50}$) (μm) | 1.32 | 1.30 | 1.27 |

Note
*1: the parenthesized value indicates the moisture absorption of powder calcined at 500° C. for 1 hour
*2: the yield was calculated from the amount of obtained powder as the anhydride

EXAMPLE 5

A beaker having a capacity of 2 l was charged with 100 g of a powder obtained by calcining sample 1-2 obtained in Example 1 at 450° C. for 2 hours, and 600 ml of water was added thereto and the powder was dispersed for 30 minutes with stirring by a magnetic stirrer. Then, hydrochloric acid of the reagent grade (concentration=36% by weight) was added in an amount of about 130 ml corresponding to 4 moles per mole of the sum of $Al_2O_3$ and $Na_2O$ in the particles, and the temperature was elevated to 95° C. and the treatment was carried out at this temperature for 2 hours. Then, the solid was separated from the mother liquor by suction filtration, washed with water in an amount about 5 times the amount of the mother liquor, dried in an electric thermostat drier maintained at 110° C. for 24 hours and pulverized by a small mill to obtain a powder of spherical silica particles.

Similarly, spherical silica particles were obtained by the treatment with hydrochloric acid of the reagent grade in an amount of 6 moles (about 200 ml) or 10 moles per mole of the sum of $Al_2O_3$.

The chemical compositions and properties of the obtained powders are shown in Table 7.

value to 11 and the treatment was conducted at 80° C. for 1 hour.

Then, the solid was recovered by filtration, washed with water, dried in an electric thermostat drier maintained at 110° C. for 24 hours and calcined at 450° C. for 2 hours. The changes of the specific surface area and moisture absorption are shown in Table 8 (sample 6-1).

Sample 2-3 (cake) obtained in Example 2 was treated in the same manner as described in Example 2. The specific surface area and moisture absorption are shown in Table 8 (sample 6-2).

TABLE 8

| | Moisture Absorption (%) | Specific Surface Area (m²/g) |
|---|---|---|
| Sample 6-1 | | |
| dried product | 11.8 | 120 |
| product calcined at 450° C. for 2 hours | 7.6 | 81 |
| Sample 6-2 | | |
| dried product | 12.9 | 113 |

TABLE 7

| | | 4 Moles of Hydro-chloric Acid | 6 Moles of Hydro-chloric Acid | 10 Moles of Hydro-chloric Acid |
|---|---|---|---|---|
| Chemical composition (% by weight) (based on product dried at 110° C.) | Ig-loss | 13.59 | 12.43 | 8.89 |
| | $SiO_2$ | 68.49 | 86.03 | 91.06 |
| | $Al_2O_3$ | 16.59 | 1.35 | 0.03 |
| | $Na_2O$ | 1.37 | 0.09 | 0.00 |
| | Total | 100.04 | 99.96 | 99.98 |
| | $SiO_2/Al_2O_3$ molar ratio | 7.02 | 117 | 5.160 |
| Specific surface are (m²/g)(BET method) | | 168 | 310 | 370 |
| Particle size (μm) by electron microscope | | 4 truly spherical | 3.8 truly spherical | 3.8 truly spherical |
| Moisture absorption (%) (90% RH × 24 hours) | | 12.7 | 18.9 | 23.7 |

EXAMPLE 6

A beaker having a capacity of 500 ml was charged with 50 g of sample 1-3 (cake) obtained in Example 1 and 300 ml of water was added thereto, and the mixture was sufficiently dispersed by a stirrer. A glass electrode of a pH water was put in the dispersion and the pH value was measured. It was found that the pH value was 4.3

Then, dilute aqueous ammonia having a concentration of 5% by weight was added to the dispersion to adjust the pH TABLE 8-continued

| | Moisture Absorption (%) | Specific Surface Area (m²/g) |
|---|---|---|
| product calcined at 450° C. for 2 hours | 8.5 | 45 |

Application Example 1

A composition comprising 100 parts by weight of a polypropylene resin having a melt flow rate of 1.9 g/10 min, 0.10 part by weight of 2,6-di-t-butyl-p-cresol, 0.05 part by weight of calcium stearate and 0.6 part by weight of the sample shown in Table 9 was mixed by a super mixer and pelletized at 230° C. Pelletization was carried out in the same manner as described above by using synthetic silica (0.8 μm) or calcium carbonate (Eskalon #1500) instead of the sample or without using any inorganic substance.

The pellets were formed into films by using an extruder and the films were drawn at a draw ratio of 6 in each of the longitudinal and lateral directions to obtain drawn films having a thickness of 30 μm.

With respect to each of the so-obtained biaxially drawn films, the transparency, blocking property and scratch resistance were determined according to the measurement methods described below. The obtained results are shown in Table 9.

(1) Transparency

The transparency was determined according to the method of ASRM D-1003.

(2) Blocking Property

Two films were piled and a load of 20 kg was imposed, and the piled films were allowed to stand still in an oven maintained at 40° C. for 24 hours. The force necessary for peeling the two films from each other was measured and designated as the blocking property.

(3) Scratch Resistance

Two films were piled and rubbed with fingers. The scratch resistance was evaluated based on the scratching degree according to the following scale:

⊚: not scratched at all
○: slightly scratched
Δ: scratched
X: considerably scratched Products obtained by calcining samples 1-3, 2-1, 2-2 and 2-3 obtained in Examples 1 and 2 at 400° C. for 1 hour (samples 1 through 4) and products obtained by surface-treating calcined samples 2-2 and 2-3 (samples 5 and 6) were used at the above-mentioned test.

The surface treatment was carried out in the following manner.

On a watch glass having a diameter of 10 cm, 50 g of the sample was thinly spread and a silane coupling agent (SH-6040 supplied by Toray Silicone) was sprayed in an amount of about 1% based on the sample by a small sprayer. Then, the sample was sufficiently stirred and treated in an electric thermostat drier maintained at 150° C. for 3 hours to obtain a surface-treated sample to be tested.

TABLE 9

| Sample No. | | Amount Added (parts by weight) | Transparency (%) | Blocking Property (kg/10 cm²) | Scratch Resistance |
|---|---|---|---|---|---|
| 1 | Sample 1-3 (400° C. × 1 hour) | 0.06 | 3.7 | 0.20 | ⊚ |
| 2 | Sample 2-1 (400° C. × 1 hour) | 0.06 | 4.1 | 0.25 | ○ |
| 3 | Sample 2-2 (400° C. × 1 hour) | 0.06 | 3.8 | 0.24 | ⊚ |
| 4 | Sample 2-3 (400° C. × 1 hour) | 0.06 | 3.5 | 0.21 | ⊚ |
| 5 | Sample 2-2 (400° C. × 1 hour), Surface-treated | 0.06 | 3.2 | 0.22 | ⊚ |
| 6 | Sample 2-3 (400° C. × 1 hour), Surface-treated | 0.06 | 2.9 | 0.21 | ⊚ |
| 7 | Synthetic silica | 0.06 | 4.3 | 0.62 | ○ |
| 8 | CaCO₃ | 0.06 | 7.8 | 0.78 | X |
| 9 | not added | 0.06 | 2.0 | 4.10 | ⊚ |

Application Sample 2

A powder foundation was prepared by using sample 1-3 obtained in Example 1.

| | |
|---|---|
| Component (A) | |
| Mica | 38 parts by weight |
| Talc | 10 parts by weight |
| Titanium oxide | 18 parts by weight |
| Coloring pigment | 5 parts by weight |
| Spherical silica (sample 1-3) | 15 parts by weight |
| Component (B) | |
| Squalene | 5.0 parts by weight |
| Lanoline | 4.0 parts by weight |
| Isopropyl myristate | 3.0 parts by weight |
| Surface active agent | 1.0 part by weight |
| Perfume | appropriate amount |

Predetermined amounts of mica, talc, titanium dioxide, coloring pigment and spherical silica of the component (A) were charged in a stainless steel vessel and sufficiently mixed, and the mixture was pulverized by an atomizer. The mixture was sufficiently blended by a Henschel mixer, and a heated mixture of the ingredients of the component (B) was added and the resulting mixture was sufficiently blended to obtain a product.

The obtained foundation and a foundation free of spherical silica were subjected to a comparison test by randomly selected twenty adults 20 to 50 years old. It was generally judged that the foundation containing spherical silica had a better spreading property and gave a smooth and plain finish and this foundation was excellent in the air permeability.

We claim:

1. Amorphous silica-alumina spherical particles composed of X-ray diffractometrically substantially amorphous silica-alumina containing less than 25% by weight of $Al_2O_3$, and less than 12% by weight of $Na_2O$, wherein individual particles have
   (a) a spherical shape having a circularity (A) represented by the following formula:

$$A = \frac{\sqrt{r1\, r2}}{r1}$$

in which r1 denotes the radius of a circumcircle of said particle and r2 denotes the radius of an inscribed circle of said particle, the circularity (A) being in the range of from 0.90 to 1, (b) a notched surface having a notching degree (B) represented by the following formula:

$$B = \frac{\Delta t}{r1} \times 100$$

in which $\Delta t$ denotes the depth between a peak and a trough in the radial direction of a notch on a cross-section of said particle and r1 is as defined above, the notching degree (B) being in the range of from 1 to 10%, and (c) a primary particle size represented by the formula 2r1, in which r1 is as defined above, in the range of from 0.1 to 20 μm, and wherein said particles having a moisture absorption smaller than 13% by weight when said particles are held in an atmosphere maintained at a temperature of 25° C. and a relatively humidity of 90% for 24 hours, said particles being obtained by acid-treating zeolite particles having an X-ray diffraction pattern inherent to the structure of P zeolite and having a spherical shape and a notched surface to remove the sodium component contained therein.

2. A filler for a polymer, which comprises amorphous silica-alumina spherical particles as set forth in claim 1 and a resin.

3. Amorphous silica-alumina spherical particles as set forth in claim 1, wherein the standard deviation of the primary particle size is smaller than 0.85.

4. Amorphous silica-alumina spherical particles as set forth in claim 1, wherein the particles have a bulk density of 0.2 to 1.2 g/ml.

5. Amorphous silica-alumina spherical particles as set forth in claim 1, wherein the particles have a BET specific surface area smaller than 400 $m^2/g$.

* * * * *